United States Patent
Runge et al.

(10) Patent No.: US 12,317,904 B2
(45) Date of Patent: Jun. 3, 2025

(54) **COMPOSITION AND PROCESS FOR PRODUCING A FERMENTED MILK PRODUCT COMPRISING APPLICATION OF A LACTOSE-DEFICIENT *S. THERMOPHILUS* STRAIN, A LACTOSE-DEFICIENT *L. BULGARICUS* STRAIN AND A PROBIOTIC STRAIN**

(71) Applicant: Chr. Hansen A/S, Hoersholm (DK)

(72) Inventors: Mette Oehrstroem Runge, Hoersholm (DK); Sonja Bloch, Hoersholm (DK); Hui Han, Beijing (CN)

(73) Assignee: Chr, Hansen A/S, Hoersholm (DK)

( * ) Notice: Subject to any disclaimer, the term of this patent is extended or adjusted under 35 U.S.C. 154(b) by 1075 days.

(21) Appl. No.: 17/050,125

(22) PCT Filed: Apr. 17, 2019

(86) PCT No.: PCT/EP2019/059876
§ 371 (c)(1),
(2) Date: Oct. 23, 2020

(87) PCT Pub. No.: WO2019/206754
PCT Pub. Date: Oct. 31, 2019

(65) Prior Publication Data
US 2021/0161163 A1    Jun. 3, 2021

(30) Foreign Application Priority Data
Apr. 24, 2018  (EP) .................................. 18168954
Sep. 12, 2018  (EP) .................................. 18194018

(51) Int. Cl.
  A23C 9/123   (2006.01)
  C12N 1/20    (2006.01)
  C12P 1/04    (2006.01)

(52) U.S. Cl.
  CPC .......... *A23C 9/1234* (2013.01); *A23C 9/1238* (2013.01); *C12N 1/20* (2013.01); *C12P 1/04* (2013.01)

(58) Field of Classification Search
  CPC ........ C12N 1/20; C12N 1/205; A23C 9/1234; A23C 9/1238; C12P 1/04; A23V 2400/165; C12R 2001/225; C12R 2001/46
  USPC .......................................................... 426/43
  See application file for complete search history.

(56) References Cited

U.S. PATENT DOCUMENTS

| 10,813,367 B2 | 10/2020 | Garrigues et al. |
| 2019/0082707 A1 | 3/2019 | Curic-Bawden et al. |
| 2019/0183160 A1 | 6/2019 | Gilleladen et al. |

FOREIGN PATENT DOCUMENTS

| WO | WO-01/88150 A1 | 11/2001 |
| WO | WO-2015/193459 A1 | 12/2015 |
| WO | WO-2017/021754 A1 | 2/2017 |
| WO | WO-2017/125600 A1 | 7/2017 |
| WO | WO-2017/194650 A1 | 11/2017 |
| WO | WO-2018/041869 A1 | 3/2018 |

OTHER PUBLICATIONS

Bovo et al, 2014, Food Science and Technology, vol. 34, No. 3 pp. 566-570.
Hedberg et al., 2008, Oral Microbiology and Immunology, vol. 23, pp. 482-485.

*Primary Examiner* — Subbalakshmi Prakash
(74) *Attorney, Agent, or Firm* — Yoshimi D. Barron

(57) ABSTRACT

The present invention relates to a composition for producing a fermented milk product showing a low degree of post-acidification during storage comprising •1) a starter culture of lactic acid bacteria comprising at least one lactose-deficient *Streptococcus thermophilus* strain, which is capable of metabolizing a non-lactose carbohydrate, and at least one lactose-deficient *Lactobacillus delbrueckii* subsp. *bulgaricus* strain, which is capable of metabolizing the non-lactose carbohydrate, and •2) a probiotic strain selected from the group consisting of *Lactobacillus* strain and a *Bifidobacterium* strain.

15 Claims, No Drawings

COMPOSITION AND PROCESS FOR PRODUCING A FERMENTED MILK PRODUCT COMPRISING APPLICATION OF A LACTOSE-DEFICIENT *S. THERMOPHILUS* STRAIN, A LACTOSE-DEFICIENT *L. BULGARICUS* STRAIN AND A PROBIOTIC STRAIN

CROSS-REFERENCE TO RELATED APPLICATIONS

The present application is the U.S. National Stage of International Application No. PCT/EP2019/059876, filed Apr. 17, 2019, and claims priority to European Patent Application Nos. 18168954.8, filed Apr. 24, 2018, and 18194018.0, filed Sep. 12, 2018.

FIELD OF THE INVENTION

The present invention relates to a composition and process for producing a fermented milk product.

BACKGROUND OF THE INVENTION

EP-A1-2 957 180 discloses a method of producing a fermented milk product using lactose-deficient lactic acid bacteria, in particular lactose-deficient *Streptococcus thermophilus* strains and *Lactobacillus delbrueckii* subsp. *bulgaricus* strains, which are capable of metabolizing a non-lactose carbohydrate.

In a milk fermentation using a starter culture containing lactose-deficient lactic acid bacteria, a non-lactose carbohydrate, such as sucrose, glucose or galactose, is added to the milk base at the start of the fermentation in an amount measured so as to become depleted at the target pH and hence result in stopping the growth of the lactic acid bacteria and in stopping the fermentation. Hereby, the post-acidification during subsequent storage is lowered significantly or even fully prevented.

However, when it is desired to produce fermented milk products containing added sucrose for sweetening the product, there is a risk that an unacceptable degree of post-acidification during storage will result, in particular at elevated temperatures.

Probiotic strains, such as *Lactobacillus rhamnosus* strain LGG® deposited as ATCC53103, are widely used in fermented milk products. However, in many fermented milk products probiotic strains will grow during storage, in particular at elevated temperatures, resulting in undesirable post-acidification.

SUMMARY OF THE INVENTION

The object of the present invention is to provide a composition for producing a fermented milk product with improved post-acidification properties.

The object of the present invention is obtained by a composition for producing a fermented milk product comprising
1) a starter culture of lactic acid bacteria comprising at least one lactose-deficient *Streptococcus thermophilus* strain, which is capable of metabolizing a non-lactose carbohydrate, and at least one lactose-deficient *Lactobacillus delbrueckii* subsp. *bulgaricus* strain, which is capable of metabolizing the non-lactose carbohydrate, and
2) a probiotic strain selected from the group consisting of *Lactobacillus* strain and a *Bifidobacterium* strain.

The present invention is based on the surprising experimental finding that when using a starter culture consisting of lactose-deficient strains in combination with the probiotic strain, the problems with respect to post-acidification associated with both the said starter culture and the said probiotic strain are strongly reduced. In particular, when a sweetening carbohydrate, such as sucrose, is added to the fermented milk product, the level of post-acidification caused by the starter culture during storage of the fermented milk product is reduced strongly. Also, the level of post-acidification caused by the probiotic strain during storage of the fermented milk product is reduced strongly.

Furthermore, in fermentation of a milk base to produce a fermented milk product the composition of the invention has a reduced fermentation time as compared to a corresponding composition containing no probiotic strain.

The present invention further relates a to process for producing a fermented milk product comprising the steps of
1) adding a starter culture of lactic acid bacteria comprising at least one lactose-deficient *Streptococcus thermophilus* strain, which is capable of metabolizing a non-lactose carbohydrate, and at least one lactose-deficient *Lactobacillus delbrueckii* subsp. *bulgaricus* strain, which is capable of metabolizing the non-lactose carbohydrate, to a milk base,
2) fermenting the milk base for a period of time until a target pH is reached to obtain a fermented milk product, and
3) adding a probiotic strain selected from the group consisting of *Lactobacillus* strain and a *Bifidobacterium* strain to the process.

DETAILED DISCLOSURE OF THE INVENTION

Lactose-Deficient Lactic Acid Bacteria

The terms "deficiency in lactose metabolism" and "lactose deficient" are used in the context of the present invention to characterize LAB which either partially or completely lost the ability to use lactose as a source for cell growth or maintaining cell viability. Respective LAB are capable of metabolizing one or several carbohydrates selected from sucrose, galactose and/or glucose or another fermentable carbohydrate. Since these carbohydrates are not naturally present in milk in sufficient amounts to support fermentation by lactose deficient mutants, it is necessary to add these carbohydrates to the milk. Lactose deficient and partially deficient LAB can be characterized as white colonies on a medium containing lactose and X-Gal.

In a particular embodiment of the invention, the lactose-deficient strain is capable of metabolizing a non-lactose carbohydrate selected from the group consisting of sucrose, galactose and glucose, preferably sucrose. In a particular embodiment of the invention, the lactose-deficient strain is capable of metabolizing galactose.

In a particular embodiment of the invention, the lactose-deficient *Streptococcus thermophilus* strain is selected from the group consisting of:
(a) (i) the strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28952;
(ii) a strain derived from DSM 28952, wherein the derived strain is further characterized as having the ability to generate white colonies on a medium containing lactose and X-Gal;
(b) (i) the strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28953;
(ii) a strain derived from DSM 28953, wherein the derived strain is further characterized as having the ability to generate white colonies on a medium containing lactose and X-Gal;
(c) (i) the strain deposited with DSMZ-Deutsche Sammlung von Mikroorganismen und Zellkulturen GmbH, Inhoffenstr. 7B, D-38124 Braunschweig, on 2017 Aug. 22 under the accession no. DSM 32599;
(ii) a strain derived from DSM 32599, wherein the derived strain is further characterized as having the ability to generate white colonies on a medium containing lactose and X-Gal; and
(d) (i) the strain deposited with DSMZ-Deutsche Sammlung von Mikroorganismen und Zellkulturen GmbH, Inhoffenstr. 7B, D-38124 Braunschweig, on 2017 Aug. 22 under the accession no. DSM 32600; and
(ii) a strain derived from DSM 32600, wherein the derived strain is further characterized as having the ability to generate white colonies on a medium containing lactose and X-Gal.

In a particular embodiment of the invention, the lactose-deficient *Streptococcus thermophilus* strain is selected from the group consisting of:
(a) (i) the strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28952;
(ii) a strain derived from DSM 28952, wherein the derived strain is further characterized as having the ability to generate white colonies on a medium containing lactose and X-Gal; and
(b) (i) the strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28953; and
(ii) a strain derived from DSM 28953, wherein the derived strain is further characterized as having the ability to generate white colonies on a medium containing lactose and X-Gal.

In a particular embodiment of the invention, the lactose-deficient *Streptococcus thermophilus* strain is selected from the group consisting of:
(c) (i) the strain deposited with DSMZ-Deutsche Sammlung von Mikroorganismen und Zellkulturen GmbH, Inhoffenstr. 7B, D-38124 Braunschweig, on 2017 Aug. 22 under the accession no. DSM 32599;
(ii) a strain derived from DSM 32599, wherein the derived strain is further characterized as having the ability to generate white colonies on a medium containing lactose and X-Gal; and
(d) (i) the strain deposited with DSMZ-Deutsche Sammlung von Mikroorganismen und Zellkulturen GmbH, Inhoffenstr. 7B, D-38124 Braunschweig, on 2017 Aug. 22 under the accession no. DSM 32600; and
(ii) a strain derived from DSM 32600, wherein the derived strain is further characterized as having the ability to generate white colonies on a medium containing lactose and X-Gal.

In a particular embodiment of the invention, the lactose-deficient *Lactobacillus delbrueckii* subsp. *bulgaricus* strain is selected from the group consisting of:
(i) the strain deposited with DSMZ-Deutsche Sammlung von Mikroorganismen and Zellkulturen GmbH, Inhoffenstr. 7B, D-38124 Braunschweig, on 2014 Jun. 12 under the accession no. DSM 28910; and
(ii) a strain derived from DSM 28910, wherein the derived strain is further characterized as having the ability to generate white colonies on a medium containing lactose and X-Gal.

Probiotic Strain

The term "probiotic bacteria" refers to viable bacteria which are administered in adequate amounts to a consumer for the purpose of achieving a health-promoting effect in the consumer. Probiotic bacteria are capable of surviving the conditions of the gastrointestinal tract after ingestion and colonize the intestine of the consumer. In a particular embodiment of the invention the probiotic strain according to the present invention is selected from the group consisting of bacteria of the genus *Lactobacillus*, such as *Lactobacillus acidophilus, Lactobacillus paracasei, Lactobacillus rhamnosus, Lactobacillus casei, Lactobacillus delbrueckii, Lactobacillus lactis, Lactobacillus plantarum, Lactobacillus reuteri* and *Lactobacillus johnsonii*, the genus *Bifidobacterium*, such as the *Bifidobacterium longum, Bifidobacterium adolescentis, Bifidobacterium bifidum, Bifidobacterium breve, Bifidobacterium animalis* subsp. *lactis, Bifidobacterium dentium, Bifidobacterium catenulatum, Bifidobacterium angulatum, Bifidobacterium magnum, Bifidobacterium pseudocatenulatum* and *Bifidobacterium infantis*, and the like.

In a particular embodiment of the invention, the probiotic *Lactobacillus* strain is selected from the group consisting of *Lactobacillus acidophilus, Lactobacillus paracasei, Lactobacillus rhamnosus, Lactobacillus casei, Lactobacillus delbrueckii, Lactobacillus lactis, Lactobacillus plantarum, Lactobacillus reuteri* and *Lactobacillus johnsonii*.

In a particular embodiment of the invention, the probiotic *Lactobacillus* strain is selected from the group consisting of a *Lactobacillus rhamnosus* strain and a *Lactobacillus paracasei* strain.

In a particular embodiment of the invention, the probiotic strain is *Lactobacillus rhamnosus* strain LGG® deposited as ATCC53103.

In a particular embodiment of the invention, the probiotic strain is *Lactobacillus paracasei* strain CRL 431 deposited as ATCC 55544.

In a particular embodiment of the invention, the probiotic *Bifidobacterium* strain is selected from the group consisting of *Bifidobacterium longum, Bifidobacterium adolescentis, Bifidobacterium bifidum, Bifidobacterium breve, Bifidobacterium animalis* subsp. *lactis, Bifidobacterium dentium, Bifidobacterium catenulatum, Bifidobacterium angulatum, Bifidobacterium magnum, Bifidobacterium pseudocatenulatum* and *Bifidobacterium infantis*.

In a particular embodiment of the invention, the probiotic *Bifidobacterium* probiotic strain is *Bifidobacterium animalis* subsp. *lactis* BB-12 deposited as DSM15954.

Composition of the Invention

In a particular embodiment, the composition contains two or more lactose-deficient *Streptococcus thermophilus* strains and one lactose-deficient *Lactobacillus delbrueckii* subsp. *bulgaricus* strain.

In a particular embodiment of the composition, the non-lactose carbohydrate is selected from the group consisting of sucrose, galactose and glucose.

In a particular embodiment of the present invention, the composition comprises from $10^4$ to $10^{12}$ CFU (colony forming units)/g of the *Streptococcus thermophilus* strain, such as from $10^5$ to $10^{11}$ CFU/g, such as from $10^6$ to $10^{10}$ CFU/g, or such as from $10^7$ to $10^9$ CFU/g of the *Streptococcus thermophilus* strain.

In a particular embodiment the composition further comprises from $10^4$ to $10^{12}$ CFU/g of the *Lactobacillus delbrueckii* subsp. *bulgaricus* strain, such as from $10^5$ to $10^{11}$ CFU/g, such as from $10^6$ to $10^{10}$ CFU/g, or such as from $10^7$ to $10^9$ CFU/g of the *Lactobacillus delbrueckii* subsp. *bulgaricus* strain.

*Lactobacillus delbrueckii* subsp. *bulgaricus*, *Streptococcus thermophilus* and other lactic acid bacteria are commonly used as starter cultures serving a technological purpose in the production of various foods, such as in the dairy industry, such as for fermented milk products. Thus, in another preferred embodiment the composition is suitable as a starter culture.

Starter cultures may be provided as frozen or dried starter cultures in addition to liquid starter cultures. Thus, in yet another preferred embodiment the composition is in frozen, freeze-dried or liquid form.

As disclosed in WO 2005/003327, it is beneficial to add certain cryoprotective agents to a starter culture. Thus, a starter culture composition according to the present invention may comprise one or more cryoprotective agent(s) selected from the group consisting of inosine-5'-monophosphate (IMP), adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any such compounds.

Process of the Invention

The present invention further relates a to process for producing a fermented milk product comprising the steps of
1) adding a starter culture of lactic acid bacteria comprising at least one lactose-deficient *Streptococcus thermophilus* strain, which is capable of metabolizing a non-lactose carbohydrate, and at least one lactose-deficient *Lactobacillus delbrueckii* subsp. *bulgaricus* strain, which is capable of metabolizing the non-lactose carbohydrate, to a milk base,
2) fermenting the milk base for a period of time until a target pH is reached to obtain a fermented milk product, and
3) adding a probiotic strain selected from the group consisting of a *Lactobacillus* strain and a *Bifidobacterium* strain to the process.

In a particular embodiment of the invention the lactose-deficient strains are capable of metabolizing a non-lactose carbohydrate selected from the group consisting of sucrose, galactose and glucose, preferably sucrose.

In a particular embodiment of the invention, the non-lactose carbohydrate is added to the milk base at the start of the fermentation step.

In a particular embodiment of the invention, the fermentation step is terminated by a method selected from the group consisting of 1) acidification of the fermented milk rendering at least one strain of the starter culture unable to grow, 2) cooling treatment and 3) depletion of the non-lactose carbohydrate.

Preferably, the non-lactose carbohydrate is added to the milk base in an amount measured so as to become depleted and hence result in stopping the growth of lactic acid bacteria and in stopping the fermentation. Preferably, the non-lactose carbohydrate is added to the milk base in an amount measured so as to become depleted at the target pH and hence result in stopping the growth of lactic acid bacteria and in stopping the fermentation.

The amount of non-lactose carbohydrate to be added to the milk base depends on a number of parameters, including the lactic acid bacteria strains used in the starter culture, the composition of the milk base, the fermentation temperature and the desired target pH. The amount of non-lactose carbohydrate to be added to the milk base can be determined by experimentation, and it is well within the skills of a skilled person to carry out such experimentation.

In a particular embodiment of the invention the target pH is between 3.2 and 4.8, more preferably between 3.6 and 4.6, more preferably between 3.8 and 4.5 and most preferably between 4.0 and 4.4.

In a particular embodiment of the invention the fermentation temperature is between 35° C. and 45° C., preferably between 37° C. and 43° C., and more preferably between 40° C. and 43° C.

In a particular embodiment of the invention the fermented milk product is not subjected to a cooling step after the end of the fermentation step and before packaging.

In a particular embodiment of the invention, the fermented milk product is packaged at a temperature between 15 and 45° C.

In a particular embodiment of the invention, the amount of added non-lactose carbohydrate is from 1 mg/g to 30 mg/g, preferably from 2 mg/g to 20 mg/g, and more preferably from 3 mg/g to 10 mg/g milk base.

In a particular embodiment of the invention, the amount of added non-lactose carbohydrate is from 0.1% to 10%, preferably from 0.2% to 8%, preferably from 0.3% to 2%, preferably from 0.4% to 1.5%, and more preferably from 0.5% to 1.2%, wherein % is (w/w) based on milk base.

In a preferred embodiment of the invention, the milk base at the start of the fermentation step has a content of lactose of between 30.0 mg/ml and 70 mg/ml, preferably between 35 mg/ml and 65 mg/ml, more preferably between 40 mg/ml and 60 mg/ml, and most preferably between 50 mg/ml and 60 mg/ml.

In a particular embodiment of the invention, the pH value of the fermented milk product is maintained within a range of 0.5 pH units, when stored after termination of the fermentation for a period of at least 7 days at a temperature of higher than 10° C.

In a particular embodiment of the invention, the pH value of the fermented milk product is maintained within a range of 0.5 pH units, preferably within a range of 0.4 pH units, preferably within a range of 0.3 pH units, preferably within a range of 0.2 pH units and most preferably within a range of 0.1 pH units, when stored after termination of the fermentation for a period of at least 7 days at a temperature of higher than 10° C.

In a particular embodiment of the invention, the pH value of the fermented milk product is maintained within a range of 0.5 pH units, when stored after termination of the fermentation for a period of at least 7 days at a temperature of higher than 4° C., preferably higher than 6° C., preferably higher than 8° C., preferably higher than 10° C., preferably higher than 12° C., preferably higher than 14° C., preferably higher than 16° C., preferably higher than 18° C., preferably higher than 20° C., preferably higher than 22° C., preferably higher than 24° C., preferably higher than 26° C., preferably higher than 28° C., and most preferably higher than 30° C.

In a particular embodiment of the invention, the pH value of the fermented milk product is maintained within a range of 0.5 pH units, preferably within a range of 0.4 pH units, preferably within a range of 0.3 pH units, preferably within a range of 0.2 pH units and most preferably within a range of 0.1 pH units, when stored after termination of the fermentation for a period of at least 7 days at a temperature of higher than 4° C., preferably higher than 6° C., preferably higher than 8° C., preferably higher than 10° C., preferably higher than 12° C., preferably higher than 14° C., preferably higher than 16° C., preferably higher than 18° C., preferably higher than 20° C., preferably higher than 22° C., preferably higher than 24° C., preferably higher than 26° C., preferably higher than 28° C., and most preferably higher than 30° C.

The probiotic strain may be added to the process at any stage of the fermentation step, including (i) at the start of the fermentation, (ii) during the fermentation, and (iii) at the end of the fermentation.

In a particular embodiment, the probiotic strain is added to the milk base at the start of the fermentation. In an alternative particular embodiment, the probiotic strain is added to milk base during the fermentation. In another alternative particular embodiment, the probiotic strain is added to fermented milk product at the end of the fermentation.

In a particular embodiment of the invention, the probiotic strain is added in a inoculation dose of at least 1.0exp06 CFU/g, preferably at least 1.0exp07 CFU/g, more preferably at least 1.0exp08 CFU/g.

In a particular embodiment of the invention, the probiotic strain is *Lactobacillus rhamnosus* strain LGG® deposited as ATCC53103, and the probiotic strain is added in an inoculation dose of at least 1.0exp06 CFU/g, preferably at least 1.0exp07 CFU/g, more preferably at least 1.0exp08 CFU/g.

It has surprisingly been found that the higher the inoculation dose of probiotic strain, e.g. LGG®, the less post-acidification during a storage period of e.g. 56 days at ambient temperature, e.g. 25° C., is observed. In particular, when an LGG® inoculation dose of 1.0exp08 CFU/g is used, post-acidification is completely avoided.

In a particular embodiment of the invention, the amount of added non-lactose carbohydrate is from 1 mg/g to 30 mg/g, preferably from 2 mg/g to 20 mg/g, and more preferably from 3 mg/g to 10 mg/g milk base.

In a particular embodiment of the invention, the amount of added non-lactose carbohydrate is from 0.1% to 10%, preferably from 0.2% to 8%, preferably from 0.3% to 2%, preferably from 0.4% to 1.5%, and more preferably from 0.5% to 1.2%, wherein % is (w/w) based on milk base.

In a particular embodiment, a sweetener is added to the process in order to produce a sweetened product. The sweetener may be added to the process at any stage of the fermentation step, including (i) at the start of the fermentation, (ii) during the fermentation, and (iii) at the end of the fermentation.

In a preferred embodiment of the invention, the milk substrate used for the fermentation with the starter culture contains a sweetener. Preferably, the sweetener is selected from the group consisting of an artificial sugar; a High Intensity Natural Sweetener; and a sugar syrup, a puree, a juice and a nectar obtained from a source selected from the group consisting of a fruit, a vegetable and a grain. Preferably, the sugar syrup is selected from the group consisting of maple syrup, a corn syrup, a glucose syrup, a high-fructose corn syrup and golden syrup.

In connection with the present invention the term "sweetener" means a natural saccharide selected from the group consisting of fructose, glucose, sucrose and mixtures thereof, an artificial sugar or a High Intensity Natural Sweetener.

Preferably, the High Intensity Natural Sweetener is a steviol glycoside, incl. stevia. Preferably, the artificial sugar is a High Intensity Artificial Sweetener selected from the group consisting aspartame, sucralose, neotame, acesulfame potassium, saccharin, advantame and cyclamates.

Most commercial fermented milk products contain an added sweetener, such as a sugar syrup or a fruit puree. Addition of the sweetener together with the other ingredients of the milk base has the advantage that an additional, separate step of addition of the sweetener may be avoided. Also, when the sweetener is added to the fermented milk product after the fermentation step, the sweetener should be heat-treated or sterilized, and it should furthermore be added to the fermented milk product in an aseptic step, which is expensive and difficult to carry out. Therefore, addition of the sweetener before the fermentation step is preferred.

In a particular embodiment of the invention, the sweetener is sucrose. In a particular embodiment of the invention, sucrose is added in an amount of from 2% (w/w) to 12% (w/w), preferably from 4% (w/w) to 11% (w/w), more preferably from 5% (w/w) to 10% (w/w), more preferably from 6% (w/w) to 9% (w/w), and most preferably from 7% (w/w) to 8% (w/w).

In a preferred embodiment of the invention, the milk base at the start of the fermentation step has a content of lactose of between 30.0 mg/ml and 70 mg/ml, preferably between 35 mg/ml and 65 mg/ml, more preferably between 40 mg/ml and 60 mg/ml, and most preferably between 50 mg/ml and 60 mg/ml.

Fermented Milk Product

The present invention further relates to a fermented milk product produced by the process of the invention.

In a particular embodiment of the invention, the fermented milk product is a product, which may be produced using a starter culture of lactic acid bacteria strain comprising at least one lactose-deficient *Streptococcus thermophiles* strain and at least one lactose-deficient *Lactobacillus delbrueckii* subsp. *bulgaricus* strain.

In a particular embodiment of the invention, the fermented milk product is selected from the group consisting of yogurt, cream cheese, sour milk, sour cream, buttermilk, fermented whey, cultured milk, Smetana, Kefir, drinking yogurt, and Yakult. Preferably, the yogurt is selected from the group consisting of set yogurt, stirred yogurt and drinking yogurt.

In a preferred embodiment of the invention, the fermented milk product contains a further food product selected from the group consisting of fruit beverage, cereal products, fermented cereal products, chemically acidified cereal products, soy milk products, fermented soy milk products and any mixture thereof.

The fermented milk product typically contains protein in a level of between 2.0% by weight to 3.5% by weight. The fermented milk product may also be a low protein product with a protein level of between 1.0% by weight and 2.0% by weight. Alternatively, the fermented milk product may be a high protein product with a protein level of above 3.5% by weight.

Use of the Invention

The present invention further relates to use in a process for producing a fermented milk product comprising the steps of
1) adding a starter culture of lactic acid bacteria comprising at least one lactose-deficient *Streptococcus thermophilus* strain, which is capable of metabolizing a non-lactose carbohydrate, and at least one lactose-deficient *Lactobacillus delbrueckii* subsp. *bulgaricus* strain, which is capable of metabolizing the non-lactose carbohydrate, to a milk base,
2) fermenting the milk base for a period of time until a target pH is reached to obtain a fermented milk product, and
3) adding a probiotic strain selected from the group consisting of *Lactobacillus* strain and a *Bifidobacterium* strain to the process, of a composition comprising
1) a starter culture of lactic acid bacteria comprising at least one lactose-deficient *Streptococcus thermophilus* strain, which is capable of metabolizing a non-lactose carbohydrate, and at least one lactose-deficient *Lactobacillus delbrueckii* subsp. *bulgaricus* strain, which is capable of metabolizing the non-lactose carbohydrate, and
2) a probiotic strain selected from the group consisting of *Lactobacillus* strain and a *Bifidobacterium* strain.

A particular embodiment of the invention relates to use to reduce the post-acidification of the fermented milk product during storage after termination of the fermentation as compared to using a corresponding starter culture with no probiotic strain.

A particular embodiment of the invention relates to use to maintain the pH value of the fermented milk product within a range of 0.5 pH units, when stored after termination of the fermentation for a period of at least 7 days at a temperature of higher than 10° C.

Definitions

In connection with the present invention the following definitions apply:

The expression "lactic acid bacteria" ("LAB") designates gram-positive, microaerophilic or anaerobic bacteria, which ferment sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. These are frequently used as food cultures alone or in combination with other lactic acid bacteria.

Lactic acid bacteria, including bacteria of the species *Lactobacillus* sp. and *Lactococcus* sp., are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product or a cheese. Such lactic acid bacterial cultures are in general referred to as "starter cultures" or "starters". Typically, a starter culture for yogurt comprises *Streptococcus thermophilus* and *Lactobacillus delbrueckii* subsp. *bulgaricus*, and in most countries a yogurt is by legislation defined as a fermented milk product produced using a starter culture comprising the two said strains.

The expression "starter culture" includes both a starter culture in the form of a mixture of all of the three strains of the composition, i.e. the lactose-deficient *Streptococcus thermophilus* strain, the lactose-deficient *Lactobacillus delbrueckii* subsp. *bulgaricus* strain, and the probiotic strain, as well as a starter culture comprising a mixture of the two strains *Streptococcus thermophilus* and *Lactobacillus delbrueckii* subsp. *bulgaricus*, wherein the probiotic strain is in separate form allowing addition of the probiotic strain to the process separately from the addition of the said two other strains.

The term "milk" is to be understood as the lacteal secretion obtained by milking of any mammal, such as cows, sheep, goats, buffaloes or camels. In a preferred embodiment, the milk is cow's milk. The term milk also includes protein/fat solutions made of plant materials, e.g. soy milk.

The term "milk base" may be any raw and/or processed milk material that can be subjected to fermentation according to the method of the invention. Thus, useful milk bases include, but are not limited to, solutions/-suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk base may originate from any mammal, e.g. being substantially pure mammalian milk, or reconstituted milk powder.

Prior to fermentation, the milk base may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk base to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of dairy products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid (such as a cheese) or liquid form (such as a fermented milk product).

The expression "fermented milk product" means a food or feed product wherein the preparation of the food or feed product involves fermentation of a milk base with a lactic acid bacterium. "Fermented milk product" as used herein includes but is not limited to products such as thermophilic fermented milk products, e.g. yoghurt, mesophilic fermented milk products, e.g. sour cream and buttermilk, as well as fermented whey.

The term "thermophile" herein refers to microorganisms that thrive best at temperatures above 35° C. The industrially most useful thermophilic bacteria include *Streptococcus* spp. and *Lactobacillus* spp. The term "thermophilic fermentation" herein refers to fermentation at a temperature above about 35° C., such as between about 35° C. to about 45° C. The term "thermophilic fermented milk product" refers to fermented milk products prepared by thermophilic fermentation of a thermophilic starter culture and include such fermented milk products as set-yoghurt, stirred-yoghurt and drinking yoghurt, e.g. Yakult.

The term "mesophile" herein refers to microorganisms that thrive best at moderate temperatures (15° C.-35° C.). The industrially most useful mesophilic bacteria include *Lactococcus* spp. and *Leuconostoc* spp. The term "mesophilic fermentation" herein refers to fermentation at a temperature between about 22° C. and about 35° C. The term "mesophilic fermented milk product" refers to fermented milk products prepared by mesophilic fermentation of a mesophilic starter culture and include such fermented milk products as buttermilk, sour milk, cultured milk, Smetana, sour cream, thick cream, cultured cream, ymer, fermented whey, Kefir, Yakult and fresh cheese, such as Quark, tvarog and cream cheese.

The term "non-lactose carbohydrate" means any carbohydrate, which is not lactose, and which a lactose-deficient lactic acid bacterium used in the process of the invention is capable of metabolizing.

The term "depletion" in relation to non-lactose carbohydrate means that the concentration of the non-lactose carbohydrate is zero or so low so that the starter culture is no longer capable of growing.

The expression "at the start of the fermentation step" means shortly before, at the same time as or shortly after addition of the starter culture to the milk base. Here, the term "shortly" means less than 30 minutes".

The expression "during the fermentation step" means at any time during the fermentation after the start and before the end of the fermentation.

The expression "at the end of the fermentation step" means shortly before, at the same time as or shortly after the target pH is reached. Here, the term "shortly" means less than 30 minutes".

The term "target pH" means the pH at which the fermentation step ends. Depending on various parameters of the process, the fermentation step is terminated by a method selected from the group consisting of 1) acidification of the fermented milk rendering at least one strain of the starter culture unable to grow, 2) cooling treatment and 3) depletion of the non-lactose carbohydrate.

In the present context, the term "mutant strain" should be understood as strains derived, or strains which can be derived from a strain (or their mother strain) of the invention by means of e.g. genetic engineering, radiation and/or chemical treatment. The "strains derived therefrom" can also be spontaneously occurring mutants. It is preferred that the "strains derived therefrom" are functionally equivalent mutants, e.g. mutants that have substantially the same, or improved properties as their mother strain. Especially, the term "mutant strains" refers to strains obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood as one mutagenization step followed by a screening/selection step), but it is presently preferred that no more than 20, or no more than 10, or no more than 5, treatments (or screening/selection steps) are carried out. In a presently preferred mutant less than 1%, less than 0.1%, less than 0.01%, less than 0.001% or even less than 0.0001% of the nucleotides in the bacterial genome have been replaced with another nucleotide, or deleted, compared to the mother strain.

Deposits and Expert Solution

The Applicant requests that a sample of the deposited microorganism should be made available only to an expert approved by the Applicant.

*Streptococcus thermophilus* strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28952.

*Streptococcus thermophilus* strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28953.

*Streptococcus thermophilus* strain deposited with DSMZ-Deutsche Sammlung von Mikroorganismen und Zellkulturen GmbH, Inhoffenstr. 7B, D-38124 Braunschweig, on 2017 Aug. 22 under the accession no. DSM 32599.

*Streptococcus thermophilus* strain deposited with DSMZ-Deutsche Sammlung von Mikroorganismen und Zellkulturen GmbH, Inhoffenstr. 7B, D-38124 Braunschweig, on 2017 Aug. 22 under the accession no. DSM 32600.

*Lactobacillus delbrueckii* subsp. *bulgaricus* strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28910;

*Bifidobacterium animalis* subsp. *lactis* strain BB-12 deposited with DSMZ-Deutsche Sammlung von Mikroorganismen und Zellkulturen GmbH, Mascheroder Weg. 1b, D-38124 Braunschweig, on 2003 Sep. 30 under the accession no. DSM 15954;

The deposits were made according to the Budapest treaty on the international recognition of the deposit of microorganisms for the purposes of patent procedure.

EXAMPLES

Example 1

Post-Acidification of Yogurt at Elevated Temperature Using Lactose-Deficient and Lactose-Positive Cultures in Combination with Probiotics The object of this experiment is to compare the effect that addition of the probiotic cultures LGG and BB-12 have with respect to post-acidification during long-term storage at room temperature for a lactose-deficient culture of the invention and a comparative lactose-positive culture.

Starter Cultures

Acidifix: Lactose-deficient culture containing lactose-deficient *Streptococcus thermophilus* strains and lactose-deficient *Lactobacillus delbrueckii* subsp. *bulgaricus* strains. Commercial strain YoFlex Acidifix 1.0 from Chr. Hansen A/S. Premium: Commercial, lactose-positive culture containing lactose-deficient *Streptococcus thermophilus* strains and lactose-positive *Lactobacillus delbrueckii* subsp. *bulgaricus* strains. Commercial strain YoFlex Premium 1.0 from Chr. Hansen A/S.

Probiotic Cultures

LGG: *Lactobacillus rhamnosus* strain LGG® deposited as ATCC53103

BB-12: *Bifidobacterium animalis* subsp. *lactis* strain BB-12 deposited as DSM 15954.

Culture Compositions

TABLE 1

|  | Sucrose (%) |
|---|---|
| Acidifix Ref. | 0.75% |
| Acidifix Ref. with sucrose before | 7.00% |
| Acidifix Ref. with sucrose after | 7.00% |
| Acidifix LGG | 0.75% |
| Acidifix LGG with sucrose before | 7.00% |
| Acidifix LGG with sucrose after | 7.00% |
| Acidifx BB-12 | 0.75% |
| Acidifix BB-12 sucrose before | 7.00% |
| Acidifix BB-12 sucrose after | 7.00% |
| Premium Ref. | 0% |
| Premium Ref. with sucrose before | 7.00% |
| Premium Ref. with sucrose after | 7.00% |
| Premium LGG | 0% |
| Premium LGG with sucrose before | 7.00% |
| Premium LGG with sucrose after | 7.00% |

Milk Bases

TABLE 2

Composition of milk bases

|  | Amount | Protein | Carbohydrate | Fat |
|---|---|---|---|---|
| 3.5% milk | 2550.0 g | 3.8% | 4.7% | 3.5% |
| Water | 450 g | 0.0% | 0.0% | 0.0% |
| Sucrose | 225 g | 0.0% | 100.0% | 0.0% |
| Milk Base 7% sucrose before | 3225 g | 3.00% | 10.70% | 2.75% |
| 3.5% milk | 2650 g | 3.8% | 4.7% | 3.5% |
| Water | 380 g | 0.0% | 0.0% | 0.0% |
| Sucrose * | 22.9 g | 0.0% | 100.0% | 0.0% |
| Milk Base 7% sucrose after (0.75% sucrose added before) | 3053 g | 3.30% | 4.84% | 3.02% |
| 3.5% milk | 2650 g | 3.8% | 4.7% | 3.5% |
| Water | 400 g | 0.0% | 0.0% | 0.0% |
| Sucrose * | 0 g | 0.0% | 100.0% | 0.0% |
| Milk Base for Premium (no sucrose) | 3050 g | 3.30% | 4.09% | 3.02% |

* 100 g sucrose solution (66%) is added per 1 L fermented milk.

Procedure

Milk fermentation was carried out in 3 L fermentor tanks at a temperature of 43° C. until an end pH of 4.55 was reached to produce yogurt. The yogurt was then cooled in a Post Treatment Unit (PTU) at 25° C. and 2 bar and transferred to 100 ml cups, which are stored at 25° C. For each yogurt with 0.75% sucrose added before fermentation, both samples with no sugar added after fermentation and samples with sugar added after fermentation (to reach a total of 7% sucrose) were stored.

Measurements

Time to reach end pH, post-acidification, and cell counts for probiotic strains were measured.

Results

Time to Reach End pH

TABLE 3

|  | Sucrose in milk base (%) | pH at end of fermentation | Time to end pH | Reduction in time (hours (h) and minutes (min.)) |
|---|---|---|---|---|
| Acidifix Ref. | 0.75% | 4.55 | 6 h 30 min. |  |
| Acidifix Ref. with sucrose before | 7.00% | 4.55 | 4 h 50 min. | 1 h 40 min. as compared to low sucrose |
| Acidifix LGG | 0.75% | 4.55 | 5 h 30 min. | 1 h as compared to no LGG |
| Acidifix LGG with sucrose before | 7.00% | 4.55 | 4 h 30 min. | 20 min. as compared to no LGG. 1 h as compared to low sucrose. |
| Acidifx BB-12 | 0.75% | 4.54 | 6 h 00 min. | 30 min. as compared to no BB-12 |
| Acidifix BB-12 sucrose before | 7.00% | 4.55 | 4 h 30 min. | 20 min. as compared to no BB-12. 1 h 30 min. as compared to low sucrose. |
| Premium Ref. | 0% | 4.54 | 5 h 30 min. |  |
| Premium Ref. with sucrose before | 7.00% | 4.53 | 5 h 00 min. | 30 min. as compared to no sucrose |
| Premium LGG | 0% | 4.55 | 5 h 15 min. | 15 min. as compared to no LGG |
| Premium LGG with sucrose before | 7.00% | 4.55 | 4 h 45 min. | 15 min. as compared to no LGG. 30 min. as compared to no sucrose |

From Table 3 the following appears:

For Acidifix (low sucrose) LGG and BB-12 reduce the fermentation time by 1 h and 30 min., respectively.

For Acidifix (7% sucrose) LGG and BB-12 both reduce the fermentation time by 20 min.

For Premium (no sucrose) LGG reduces the fermentation time by 15 min.

For Premium (7% sucrose) LGG reduces the fermentation time by 15 min.

In conclusion, for the Acidifix culture LGG reduces the fermentation time significantly more than LGG reduces the fermentation time for the Premium culture.

Post-Acidification

TABLE 4

| | Sucrose (%) | pH Day 7, 25° C. |
|---|---|---|
| Acidifix Ref. | 0.75% | 4.37 |
| Acidifix Ref. with sucrose before | 7.00% | 4.34 |
| Acidifix Ref. with sucrose after | 7.00% | 4.34 |
| Acidifix LGG | 0.75% | 4.27 |
| Acidifix LGG with sucrose before | 7.00% | 4.16 |
| Acidifix LGG with sucrose after | 7.00% | 4.20 |
| Acidifx BB-12 | 0.75% | 4.38 |
| Acidifix BB-12 sucrose before | 7.00% | 4.35 |
| Acidifix BB-12 sucrose after | 7.00% | 4.36 |
| Premium Ref. | 0% | 4.29 |
| Premium Ref. with sucrose before | 7.00% | 4.19 |
| Premium Ref. with sucrose after | 7.00% | 4.26 |
| Premium LGG | 0% | 4.00 |
| Premium LGG with sucrose before | 7.00% | 3.96 |
| Premium LGG with sucrose after | 7.00% | 3.99 |

TABLE 5

| Difference in pH at Day 7, 25° C. between | Acidifix | Premium |
|---|---|---|
| Culture Ref. and Culture with sucrose before | 0.03 | 0.10 |
| Culture Ref. and Culture with sucrose after | 0.03 | 0.03 |
| Culture Ref. and Culture LGG | 0.10 | 0.29 |
| Culture Ref. and Culture BB-12 | +0.01 | ND |
| Culture Ref. sucrose before and Culture LGG sucrose before | 0.18 | 0.23 |
| Culture Ref. sucrose after and Culture LGG sucrose after | 0.14 | 0.27 |
| Culture Ref. sucrose before and Culture BB-12 sucrose before | +0.01 | ND |
| Culture Ref. sucrose after and Culture BB-12 sucrose after | +0.02 | ND |

As will appear from Table 5, the effect of LGG addition on post-acidification is significantly less for the Acidifix culture than for the Premium culture at Day 7, 255° C. Furthermore, for the combination of Acidifix culture and BB-12, the addition of BB-12 has no effect on post-acidification at all.

Also, for the combination of Acidifix culture and LGG, the effect of adding sucrose before fermentation is only marginally higher than when adding sucrose after fermentation, and the effect is less than for the combination of Premium culture and LGG. This shows that when using a combination of the Acidifix culture and LGG it is in fact possible to add sucrose in a highly excess amount before fermentation and still maintain an acceptable low level of post-acidification during storage. The same is true for the combination of Acidifix culture and BB-12.

Probiotic Cell Counts

TABLE 6

| | LGG (CFU/ml) | BB-12 (CFU/ml) |
|---|---|---|
| Acidifix LGG | 2.5E08 | |
| Acidifix LGG with sucrose before | 2.7E08 | |
| Acidifix LGG with sucrose after | 1.8E08 | |
| Acidifx BB-12 | | 1.6E07 |
| Acidifix BB-12 sucrose before | | 1.8E07 |
| Acidifix BB-12 sucrose after | | 1.3E07 |
| Premium LGG | 3.6E08 | |
| Premium LGG with sucrose before | 3.3E08 | |
| Premium LGG with sucrose after | 1.9E08 | |

Example 2

Post-Acidification of Yogurt Using Lactose-Deficient and Lactose-Positive Cultures in Combination with Probiotics The object of this experiment is to compare the effect that addition of the probiotic culture LGG has with respect to post-acidification during long-term storage at refrigerated and room temperatures for a lactose-deficient culture of the invention and a comparative lactose-positive culture.

Milk Base

TABLE 7

| | Composition of milk base | | | | |
|---|---|---|---|---|---|
| | Amount | Protein | Carbohydrate | Fat | Sucrose |
| 3.5% milk | 3500 g | 3.4% | 4.7% | 3.5% | |
| Water | 200 g | 0.0% | 0.0% | 0.0% | |
| Sucrose | 278 g | 0.0% | 100.0% | 0.0% | |
| Milk Base 7% sucrose | 3978 g | 2.99% | 11.12% | 3.08% | 6.99% |

Starter Cultures

Acidifix: Lactose-deficient culture containing lactose-deficient *Streptococcus thermophilus* strains and lactose-deficient *Lactobacillus delbrueckii* subsp. *bulgaricus* strains. Commercial strain YoFlex Acidifix 1.0 from Chr. Hansen A/S. Premium: Commercial, lactose-positive culture containing lactose-deficient *Streptococcus thermophilus* strains and lactose-positive *Lactobacillus delbrueckii* subsp. *bulgaricus* strains. Commercial strain YoFlex Premium 1.0 from Chr. Hansen A/S.

Probiotic Cultures

LGG: *Lactobacillus rhamnosus* strain LGG® deposited as ATCC53103

Culture Compositions

TABLE 8

| |
|---|
| Acidifix |
| Premium |
| Acidifix + LGG |
| Premium + LGG |

Procedure

Milk fermentation was carried out in 3 L fermentor tanks at a temperature of 43° C. until an end pH of 4.55 was reached to produce yogurt. The yogurt was then cooled in a Post Treatment Unit (PTU) at 4° C. and 2 bar and transferred to 120 ml cups, which are stored at 4° C. and 25° C.

Measurements

Post-acidification and cell counts for probiotic strains were measured.

Results

Post-Acidification

TABLE 9

|  | pH Day 14, 4° C. | pH Day 14, 21° C. |
| --- | --- | --- |
| Acidifix | 4.52 | 4.15 |
| Premium | 4.36 | 4.02 |
| Acidifix + LGG | 4.49 | 4.15 |
| Premium + LGG | 4.08 | 3.97 |

TABLE 10

| Difference in pH between | pH Day 14, 4° C. | pH Day 14, 21° C. |
| --- | --- | --- |
| Acidifix and Acidifix + LGG | 0.03 | 0.00 |
| Premium and Premium + LGG | 0.28 | 0.05 |

As will appear from Table 10, the effect of LGG addition on post-acidification is significantly less for the Acidifix culture than for the Premium culture at both 4° C. and 21° C.

Probiotic Cell Counts

TABLE 11

|  | LGG (CFU/g) Day 14, 4° C. | LGG (CFU/g) Day 14, 21° C. |
| --- | --- | --- |
| Acidifix + LGG | 2.3E07 | 2.6E08 |
| Premium + LGG | 2.7E07 | 2.7E08 |

Example 3

Post-Acidification of Yogurt at Elevated Temperature Using Lactose-Deficient Cultures in Combination with Probiotics at Different Inoculation Doses The object of this experiment is to compare the effect that addition of different inoculation doses of the probiotic culture LGG has with respect to post-acidification during long-term storage at room temperatures for a lactose-deficient culture of the invention.

TABLE 12

| Composition of milk base | | | | | |
| --- | --- | --- | --- | --- | --- |
|  | Amount (g) | Protein (%) | Carbohydrate (%) | Fat (%) | Sucrose |
| 3.4% milk | 11910 | 3.0 | 4.6 | 3.4% | |
| Water | 0.0 | 0.0 | 0.0 | 0.0 | |
| Sucrose | 90 | 0.0 | 100 | 0.0 | |
| Milk Base 0.75% sucrose | 12000 | 2.98 | 4.56 | 3.37 | 0.75% |

Starter Cultures

Acidifix: Lactose-deficient culture containing lactose-deficient *Streptococcus thermophilus* strains and lactose-deficient *Lactobacillus delbrueckii* subsp. *bulgaricus* strains. Commercial strain YoFlex Acidifix 1.0 from Chr. Hansen A/S.

Probiotic Cultures

LGG: *Lactobacillus rhamnosus* strain LGG® deposited as ATCC53103

Culture Compositions

TABLE 13

| Acidifix |
| --- |
| Acidifix + LGG (10exp06 CFU/g) |
| Acidifix + LGG (10exp07 CFU/g) |
| Acidifix + LGG (10exp08 CFU/g) |

Procedure

Milk fermentation was carried out in 1 L SCHOTT blue cap bottles at a temperature of 43° C. When the sucrose in the sample with Acidifix and no LGG was used up (pH 4.39), the fermentation of all samples was stopped. The bottles were shaken to break the curd and then stored at 4° C. to cool down. The following day, the yogurt samples were transferred aseptically to 120 ml cups, which were stored at 25° C. for 56 days.

Measurements

Post-acidification and cell counts for probiotic strains were measured.

Results

Post-Acidification

TABLE 14

| pH | Acidifix | Acidifix + LGG (10exp06 CFU/g) | Acidifix + LGG (10exp07 CFU/g) | Acidifix + LGG (10exp08 CFU/g) |
| --- | --- | --- | --- | --- |
| 1 Day | 4.39 | 4.39 | 4.38 | 4.34 |
| 7 Days | 4.41 | 4.16 | 4.19 | 4.32 |
| 14 Days | 4.41 | 4.17 | 4.20 | 4.43 |
| 21 Days | 4.42 | 4.19 | 4.22 | 4.43 |

TABLE 14-continued

| pH | Acidifix | Acidifix + LGG (10exp06 CFU/g) | Acidifix + LGG (10exp07 CFU/g) | Acidifix + LGG (10exp08 CFU/g) |
|---|---|---|---|---|
| 28 Days | 4.43 | 4.20 | 4.26 | 4.44 |
| 35 Days | 4.44 | 4.23 | 4.27 | 4.47 |
| 42 Days | 4.41 | 4.21 | 4.25 | 4.42 |
| 49 Days | 4.41 | 4.19 | 4.26 | 4.39 |
| 56 Days | 4.43 | 4.20 | 4.27 | 4.35 |

Probiotic Cell Counts

TABLE 15

| LGG cell count (CFU/g) | Acidifix | Acidifix + LGG (10exp06 CFU/g) | Acidifix + LGG (10exp07 CFU/g) | Acidifix + LGG (10exp08 CFU/g) |
|---|---|---|---|---|
| 0 Day | 0.00E00 | 1.00E06 | 8.30E06 | 9.70E07 |
| 1 Day | 0.00E00 | 1.60E06 | 1.35E07 | 1.39E08 |
| 7 Days | 0.00E00 | 4.29E08 | 3.44E08 | 4.30E08 |
| 14 Days | 0.00E00 | 5.70E08 | 5.05E08 | 8.75E08 |
| 21 Days | 0.00E00 | 5.70E08 | 6.15E08 | 5.55E08 |
| 28 Days | 0.00E00 | 4.45E08 | 4.35E08 | 3.80E08 |
| 35 Days | 0.00E00 | 6.20E07 | 1.29E08 | 1.78E08 |
| 42 Days | 0.00E00 | 5.85E07 | 1.04E08 | 1.68E08 |
| 49 Days | 0.00E00 | 6.05E07 | 1.72E08 | 2.11E08 |
| 56 Days | 0.00E00 | 7.75E07 | 1.69E08 | 1.70E08 |

As will appear from Table 15, the level of the LGG culture is maintained at a high level during the full storage period of 56 days at 25° C. Also, as will appear from Table 14, the higher the inoculation dose of LGG, the less post-acidification during the storage period of 56 days are observed. In particular, when an LGG inoculation dose of 1.0exp08 CFU/g is used, post-acidification is completely avoided.

The invention claimed is:

1. A composition for producing a fermented milk product with a low degree of post-acidification during storage, comprising:
   (A) a starter culture of lactic acid bacteria comprising
      (i) at least one lactose-deficient *Streptococcus thermophilus* strain capable of metabolizing a non-lactose carbohydrate, wherein the non-lactose carbohydrate is sucrose, glucose, or galactose, and
      (ii) at least one lactose-deficient *Lactobacillus delbrueckii* subsp. *bulgaricus* strain capable of metabolizing the non-lactose carbohydrate, and
   (B) the probiotic *Lactobacillus rhamnosus* strain deposited as ATCC53103;
wherein the pH value of the fermented milk product is maintained within a range of 0.5 pH units when stored after termination of the fermentation for a period of at least 7 days at a temperature of higher than 10° C., and wherein post-acidification during storage is reduced compared to a fermented milk product produced without said starter culture and probiotic strain.

2. A composition according to claim 1, wherein the *Streptococcus thermophilus* lactose-deficient strain is selected from the group consisting of:
   (a) (i) the strain deposited as—DSM 28952;
   (a) (ii) a strain derived from DSM 28952, wherein the derived strain generates white colonies on a medium containing lactose and X-Gal;
   (b) (i) the strain deposited as DSM 28953;
   (b) (ii) a strain derived from DSM 28953, wherein the derived strain generates white colonies on a medium containing lactose and X-Gal;
   (c) (i) the strain deposited as DSM 32599;
   (c) (ii) a strain derived from DSM 32599, wherein the derived strain generates white colonies on a medium containing lactose and X-Gal; and
   (d) (i) the strain deposited as DSM 32600; and
   (d) (ii) a strain derived from DSM 32600, wherein the derived strain generates white colonies on a medium containing lactose and X-Gal.

3. A composition according to claim 1, wherein the lactose-deficient *Lactobacillus delbrueckii* subsp. *bulgaricus* strain is selected from the group consisting of:
   (i) the strain deposited as DSM 28910; and
   (ii) a strain derived from DSM 28910, wherein the derived strain generates white colonies on a medium containing lactose and X-Gal.

4. A process for producing a fermented milk product with a low degree of post-acidification during storage, comprising:
   (A) adding to a milk base a starter culture of lactic acid bacteria comprising at least one lactose-deficient *Streptococcus thermophilus* strain capable of metabolizing a non-lactose carbohydrate, wherein the non-lactose carbohydrate is sucrose, glucose, or galactose, and at least one lactose-deficient *Lactobacillus delbrueckii* subsp. *bulgaricus* strain capable of metabolizing the non-lactose carbohydrate, and
   (B) fermenting the milk base for a period of time until a target pH is reached, to obtain a fermented milk product, and
   (C) adding the probiotic *Lactobacillus rhamnosus* strain deposited as ATCC53103 to the milk base or fermented milk product,
   wherein the pH value of the fermented milk product is maintained within a range of 0.5 pH units, when stored after termination of the fermentation for a period of at least 7 days at a temperature of higher than 10° C., and wherein post-acidification during storage is reduced compared to a fermented milk product produced without said starter culture and probiotic strain.

5. A process according to claim 4, wherein the probiotic strain is added to the milk base at the start of the fermentation step.

6. A process according to claim 4, further comprising adding the non-lactose carbohydrate to the milk base at the start of the fermentation step.

7. A process according to claim 6, wherein the non-lactose carbohydrate is added to the milk base in an amount measured so as to become depleted at the target pH and hence result in stopping the growth of the lactic acid bacteria and in stopping the fermentation.

8. A process according to claim 4, wherein the *Streptococcus thermophilus* lactose-deficient strain is selected from the group consisting of:
   (a) (i) the strain deposited as DSM 28952;
   (a) (ii) a strain derived from DSM 28952, wherein the derived strain generates white colonies on a medium containing lactose and X-Gal;
   (b) (i) the strain deposited as DSM 28953;
   (b) (ii) a strain derived from DSM 28953, wherein the derived strain generates white colonies on a medium containing lactose and X-Gal;

(c) (i) the strain deposited as DSM 32599;
(c) (ii) a strain derived from DSM 32599, wherein the derived strain generates white colonies on a medium containing lactose and X-Gal; and
(d) (i) the strain deposited as DSM 32600; and
(d) (ii) a strain derived from DSM 32600, wherein the derived strain generates white colonies on a medium containing lactose and X-Gal.

9. A process according to claim 4, wherein the lactose-deficient *Lactobacillus delbrueckii* subsp. *bulgaricus* strain is selected from the group consisting of:
   (i) the strain deposited as DSM 28910; and
   (ii) a strain derived from DSM 28910, wherein the derived strain generates white colonies on a medium containing lactose and X-Gal.

10. A process according to claim 4, wherein the probiotic *Lactobacillus rhamnosus* strain deposited as ATCC53103 is added to the milk base in an inoculation dose of at least $1.0 \times 10^6$ colony forming units (CFU)/g.

11. A fermented milk product produced by the process of claim 4.

12. A composition according to claim 1, wherein the *Streptococcus thermophilus* lactose-deficient strain is selected from the group consisting of:
   (a) the strain deposited as—DSM 28952; and
   (b) a strain derived from DSM 28952, wherein the derived strain generates white colonies on a medium containing lactose and X-Gal.

13. A composition according to claim 1, wherein the *Streptococcus thermophilus* lactose-deficient strain is selected from the group consisting of:
   (a) the strain deposited as DSM 28953; and
   (b) a strain derived from DSM 28953, wherein the derived strain generates white colonies on a medium containing lactose and X-Gal.

14. A composition according to claim 1, wherein the *Streptococcus thermophilus* lactose-deficient strain is selected from the group consisting of:
   (a) the strain deposited as DSM 32599; and
   (b) a strain derived from DSM 32599, wherein the derived strain generates white colonies on a medium containing lactose and X-Gal.

15. A composition according to claim 1, wherein the *Streptococcus thermophilus* lactose-deficient strain is selected from the group consisting of:
   (a) the strain deposited as DSM 32600; and
   (b) a strain derived from DSM 32600, wherein the derived strain generates white colonies on a medium containing lactose and X-Gal.

\* \* \* \* \*